United States Patent [19]

Birch et al.

[11] Patent Number: 4,748,123

[45] Date of Patent: May 31, 1988

[54] CONTINUOUS FERMENTATION DEVICE

[75] Inventors: John R. Birch, High Wycombe; Robert C. Boraston, Reading, both of England

[73] Assignee: Celltech Limited, Slough, England

[21] Appl. No.: 26,906

[22] PCT Filed: Jun. 20, 1986

[86] PCT No.: PCT/GB86/00360

§ 371 Date: Feb. 19, 1987

§ 102(e) Date: Feb. 19, 1987

[87] PCT Pub. No.: WO86/07604

PCT Pub. Date: Dec. 31, 1986

[30] Foreign Application Priority Data

Jun. 20, 1985 [GB] United Kingdom ............... 8515636

[51] Int. Cl.⁴ .................................. C12N 1/02
[52] U.S. Cl. ............................ 435/261; 435/286; 435/311; 435/314; 210/629
[58] Field of Search ............... 435/284, 286, 287, 299, 435/311, 312, 313, 314, 309, 315, 261, 161; 261/123; 422/227, 231; 210/195.3, 197, 629

[56] References Cited

U.S. PATENT DOCUMENTS

| | | | |
|---|---|---|---|
| 2,083,348 | 6/1932 | Scholler et al. | 435/314 |
| 2,188,192 | 1/1940 | Scholler et al. | 435/314 |
| 2,451,156 | 1/1948 | DeMattos . | |
| 3,476,366 | 11/1969 | Brooks et al. | 435/314 |
| 3,732,148 | 5/1973 | Franchowiak et al. | 435/314 |
| 3,915,807 | 10/1975 | Boiko et al. | 435/314 |
| 3,963,581 | 6/1976 | Gialobbe et al. | 435/314 |
| 4,183,787 | 1/1980 | Roester et al. | 435/314 |
| 4,218,538 | 8/1980 | Church | 435/311 |
| 4,282,328 | 8/1981 | Fakuda et al. | 435/314 |
| 4,482,458 | 11/1984 | Rovel et al. | 435/314 |
| 4,545,945 | 10/1985 | Präe et al. | 435/314 |
| 4,649,117 | 3/1987 | Familletti | 435/313 |

FOREIGN PATENT DOCUMENTS

| | | |
|---|---|---|
| 0046681 | 8/1982 | European Pat. Off. . |
| 0191356 | 8/1986 | European Pat. Off. . |
| 821326 | 2/1937 | France . |
| 57-189243 | 2/1982 | Japan . |
| 58-115137 | 1/1985 | Japan . |
| 81/02308 | 2/1981 | PCT Int'l Appl. . |
| 189396 | 3/1937 | Switzerland . |
| 448689 | 8/1936 | United Kingdom . |
| 486481 | 6/1938 | United Kingdom . |
| 0703567 | 12/1979 | U.S.S.R. ............... 435/314 |

Primary Examiner—Samuel Scott
Assistant Examiner—Noah P. Kamen
Attorney, Agent, or Firm—Spencer & Frank

[57] ABSTRACT

A continuous fermentation device for receiving a suspension culture of cells includes a fermentation vessel having inlet means to deliver suspension culture medium; baffle means defining, in combination with interior walls of said vessel, a downcomer and a riser; pump means for forcing a suspension culture to circulate in the riser and downcomer; a portion of said baffle means further defining a static settling zone disposed within said vessel, wherein said zone is surrounded by at least one of said riser and said downcomer, said zone having a bottom opening communicating with at least one of said riser and downcomer, and a top opening connected to outlet means to draw off culture supernatant, and wherein said zone provides for cells to settle out in its bottom so as to result in a cell concentration lower in the supernatant than in the suspension. The device may be employed in a method for the suspension culture of cells by culturing cells therein.

10 Claims, 2 Drawing Sheets

CONTINUOUS FERMENTATION DEVICE

BACKGROUND OF THE INVENTION

1. Field of the Invention

This invention relates to a continuous fermenter vessel for receiving an agitated suspension culture of cells.

2. Description of the Related Art

Recent advances in the commercialisation of products produced by the in vitro fermentation of cells have led to a growing interest in the design of improved fermenter vessels and fermentation processes.

Fermentation is usually carried out either in a batch process or in a continuous process. Continuous processes are advantageous since they enhance the productivity of a given fermenter and reduce the nonproductive downtime necessary for cleaning and sterilisation which is normally required in a batch fermenter.

In known continuous fermenter vessels, a suspension of cells in an appropriate culture medium is agitated and maintained at a suitable temperature for fermentation. Suspension culture is continuously withdrawn from the fermenter, balanced by a continuous supply of fresh culture medium. A significant disadvantage of such fermenters is the continual loss of cells caused by the removal of culture. Fermenters are known in which removed suspension culture is passed through a continuous centrifugal separation device which separates cells from the culture supernatant. The cells are then fed back into the suspension culture.

In another known fermenter, a rotating basket of a filter material is provided, partially submerged in the culture, such that the inside of the basket is separated from the suspension culture by the filter. Culture supernatant passes through the filter and may be withdrawn continuously, whilst cells remain in the suspension culture. The rotation of the basket in the suspension culture reduces clogging of the filter material.

These known devices for providing cell feedback in continuous suspension cultures are complicated mechanically, require energy for their operation and may cause detrimental effects, such as cell rupture, upon the suspension culture. These features combine to reduce the economic viability of fermentation processes based on such fermenters.

SUMMARY OF THE INVENTION

The object of the present invention is to provide a continuous fermenter vessel which substantially overcomes these disadvantages.

According to the present invention there is provided a continuous fermenter vessel for receiving a suspension culture of cells, the vessel comprising; means for agitating a suspension culture received in a first portion of the vessel; a second portion of the vessel defining, in use, a static settling zone, at least part of the bottom of the second portion communicating with the first portion; an inlet means for the continuous supply of culture medium to the vessel; and an outlet for the continuous withdrawal of culture supernatant from the second portion of the vessel from a point spaced above the bottom of the second portion wherein, in use, cells settling in the second portion are returned to the agitated suspension culture, and culture supernatant having a lower concentration of cells than the suspension culture is withdrawn from the second portion.

According to the present invention there is thus provided a continuous fermentation device for receiving a suspension culture of cells, the device comprising: a fermentation vessel having inlet means to deliver suspension culture medium; baffle means defining, in combination with interior walls of said vessel, a downcomer and a riser; pump means for forcing a suspension culture to circulate in the riser and downcomer; a portion of said baffle means further defining a static settling zone disposed within said vessel, wherein said zone is surrounded by at least one of said riser and said downcomer, said zone having a bottom opening communicating with at least one of said riser and downcomer, and a top opening connected to outlet means to draw off culture supernatant, and wherein said zone provides for cells to settle out in its bottom so as to result in a cell concentration lower in the supernatant than in the suspension.

In the fermenter, i.e., the continuous fermentation device, of the invention, the cell separation and cell feedback steps are achieved by the provision of a static settling zone. Suspension culture entering the static settling zone (replacing culture supernatant removed from the static settling zone) moves from the agitated suspension culture into a zone of low turbulence. In this zone, the cells begin to settle downwardly under the influence of gravity and, at the bottom of the static settling zone, are returned to the agitated suspension culture. The settling results in a cell concentration gradient within the static settling zone allowing the removal of culture supernatant from a point spaced above the bottom of the static settling zone. The culture supernatant at this point has a substantially lower cell concentration than the agitated suspension culture. The cell separation and feedback components of the fermenter of the invention have no moving parts and require no additional energy input.

The static settling zone may be situated anywhere within the fermenter or may form an appendage to the portion of the vessel for retaining, in use, the agitated suspension culture. However, in order to minimise movement within the static settling zone, it is preferred that the static settling zone is located entirely within the portion of the fermenter for retaining, in use, the agitated suspension culture. This significantly reduces temperature gradients within the static zone which may give rise to undesirable convection currents.

The means for agitating the suspension culture may be any suitable means for ensuring mixing of the cells. A suitable means is, for example, a mechanical stirrer. However, in a preferred form of the invention, agitation is caused by the injection of a gas, suitably air, through a gas inlet. The fermenter may be, for example, a so called "air-lift" fermenter in which a gas such as air is injected into an upwardly extending part of the fermenter known in the art as a riser. The riser communicates at top and bottom with the top and bottom respectively of a further upwardly extending part of the fermenter known in the art as a downcomer. A known configuration of an air-lift fermenter comprises a central divider in the fermenter vessel separating the vessel into two parts (riser and downcomer). An alternative configuration of air-lift fermenter comprises a draught tube substantially concentric with a cylindrical fermenter vessel, dividing the fermenter into a riser (within the draught tube) and a downcomer (in the annular space between the draught tube and the side of the fermenter vessel). (The riser could equally be the annular space between the draught tube and the inside of the fermentervessel, and the downcomer could be within the draught tube). The injection of a gas, such as air, into a lower part of the riser causes a reduction in the bulk density within the riser resulting in an upward flow of liquid in the riser, thus displacing the contents of the downcomer which circulates back into the bottom of the riser. In this way a fluid flow is caused, mixing the culture and maintaining the cells in suspension. The advantages of such a fermenter are that no moving parts are necessary and oxygenation of the culture occurs. Typically the cross-sectional area of the riser is substantially the same as the cross-sectional area of the downcomer.

In a preferred aspect of the invention the continuous fermenter vessel is an air-lift fermenter and the static settling zone comprises a conduit formed in a divider between a downcomer and a riser. In this way unwanted convection currents are prevented by ensuring that the static settling is surrounded by the well mixed suspension culture having a homogenous temperature. In use the working liquid level in the fermenter preferably is such that the top of the settling zone is covered by from 0.25 to 1.0 times the diameter of fermenter.

The divider may be, for example, a substantially cylindrical draught tube positioned substantially concentrically in a substantially cylindrical fermenter vessel. The static settling zone may comprise an annular space formed between inner and outer walls of at least a portion of the draught tube. The static settling zone is preferably closed at the top and communicates at the bottom with the downcomer. In air-lift fermenters of small volume for example less than ten liters, the draught tube may be double-walled along its length, forming an annular settling zone closed at the top, and communicating at the bottom with the suspension culture. Alternatively, and in particular for larger fermenters the static settling zone may comprise an annular space between inner and outer walls of an upper part of the draught tube only. In large fermenters the static settling zone must have a sufficiently large cross-sectional area so that the velocity of the upward flowing liquid is less than the settling velocity of the cells, to achieve good cell separation. To accommodate the cross-sectional area required for the static settling zone and still provide sufficient area for circulation around the vessel, an upper section of the fermenter may have a greater diameter relative to a lower section of the fermenter. The cross-sectional areas of the riser and downcomer in the upper section are substantially identical and may have a cross-sectional area of between 0.5 and 1.0 times the cross-sectional area of the riser and the downcomer respectively in the bottom section of the fermenter. To achieve this, the internal diameter of the concentric draught tube in an upper portion may be reduced relative to a lower portion of the draught tube. The upper and lower sections of the fermenter may be connected with frustoconical section having an angle of between 0° and 60° to the general axis of the fermenter.

The divider may take the form of a draught plate comprising a substantially vertical plate mounted in the vessel. The static settling zone may comprise a conduit formed in the plate either in an upper portion of the plate or along its length.

The continuous fermenter may be operated in known fashion using a continuous supply of culture medium and withdrawing continuously culture supernatant. The continuous fermenter may be operated continuously at a dilution rate (i.e. ratio of flow rate to fermenter volume) of between 0.02 hr$^{-1}$ and 0.08 hr$^{-1}$, preferably about 0.042 hr$^{-1}$.

The fermenter may be used for the culture of any cells, capable of in vitro growth in suspension liquid culture, (including microcarrier culture), but is especially useful for the culture of animal cells such as, for example, hybridoma cell lines.

It has been determined that animal cells will sediment under gravity at a rate of between $0.9 \times 10^{-5}$ ms$^{-1}$ and $4.0 \times 10^{-5}$ ms$^{-1}$ and usually about $1.8 \times 10^{-5}$ ms$^{-1}$. In order therefore to allow for a reasonable balance of high continuous throughput and small size of static settling zone, a static settling zone having a transverse cross-sectional area of from 0.1 to 1.5 m$^2$ per m$^3$ of fermenter volume is preferred. Usually a static settling zone having a transverse cross-sectional area of 0.65 m$_2$ per m$^3$ of fermenter volume is used.

Animal cells in culture can exhibit a range of particle sizes representing the difference between complete growing cells, whole dead cells and cell fragments and hence will settle at a range of rates. In order to increase the overall rate of settling within the settling zone it is possible to culture the cells in a state of flocculation, for instance, by the addition of between 0.01 and 0.3% (w/v) of a polygalacturonic acid to the culture medium. This treatment causes the cells and cell fragments to aggregate into flocs of a greater overall particle size than individual cellular particles, thus resulting in an increased rate of settling. This phenomenon enables the cross-sectional area of the settling zone to be reduced and hence enables the diameter of the upper section of the fermenter also to be reduced.

BRIEF DESCRIPTION OF THE DRAWING

The invention is now illustrated by the following description with reference to the accompanying schematic drawings in which.

DESCRIPTION OF THE PREFERRED EMBODIMENTS

Figure 1:
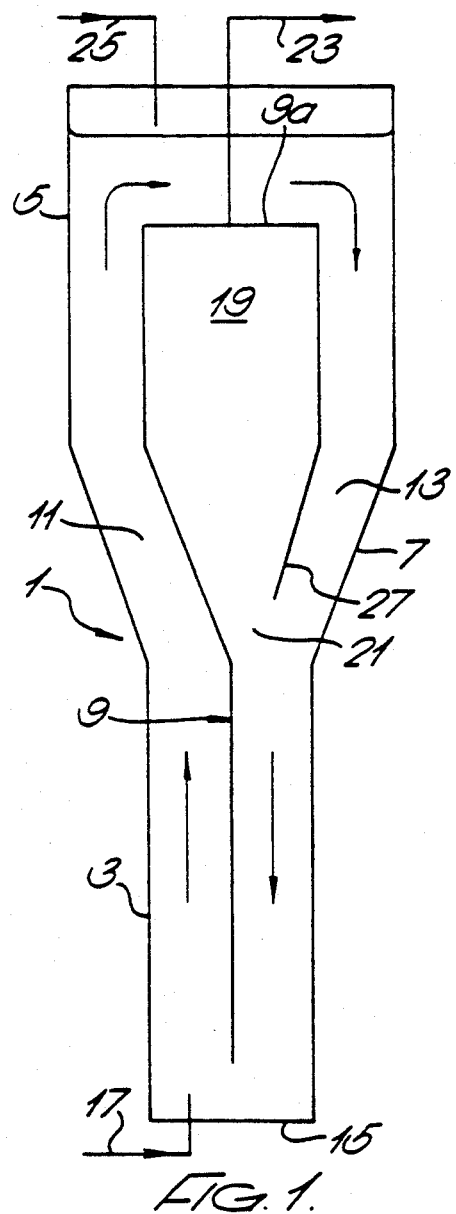
FIG. 1 is an axial cross-section of an air-lift fermenter of the invention including a central divider plate.

FIG. 1 shows a continuous fermentation device which is an air-lift fermenter incorporating a static settling zone for separating culture supernatant from suspension culture. The air-lift fermenter comprises an outer vessel, shown generally at 1. The outer vessel comprises a lower cylindrical portion 3 and an upper cylindrical portion 5, the upper cylindrical portion being of greater diameter and connected to the lower cylindrical portion 3 by a frustoconical portion 7. The lower cylindrical portion 3 is provided with a base 15 to complete the outer vessel 1. A divider plate, shown generally at 9, is supported within the outer vessel 1 to divide the interior of the vessel into a riser, shown generally at 11, and a downcomer, shown generally at 13. The base 15 carries an air inlet 17 directly below and approximately centrally within the riser 11 which functions as a pump to force suspension culture to circulate in the riser and downcomer. The divider plate, shown generally at 9, functions as a baffle and forms a static settling zone 19 in the upper cylindrical portion 5 and frustoconical portion 7 of the outer vessel. The static settling zone 19, which is rectangular in axial cross-section, is sealed from the riser 11 and downcomer 13 with the exception of a port or bottom opening 21 at the bottom of the static settling zone 19, which communicates with the downcomer 13 in the embodiment of FIG. 1. The top of the static settling zone 19 is provided with an outlet or top opening 23 for withdrawing culture supernatant. The fermenter is provided with an inlet 25 for supplying culture medium to the fermenter. Thermostatically controlled heating means may be provided either in or around the outer vessel 1. The outer vessel 1 may be double-walled to provide a jacket, for example filled with water.

In use, a suspension culture of cells, suitably animal cells, is introduced into the fermenter through inlet 25 such that the top of the divider plate 9, designated 9a is covered by a depth of suspension culture corresponding to from 0.25 to 1.0 times the diameter of the lower cylindrical portion 3 of the outer vessel 1. The suspension culture is maintained in a turbulent flow condition by forcing air through air inlet 17. The air rises within the riser 11, reducing the bulk density of the liquid suspension in the riser 11 and causing a gross movement of liquid in the direction indicated by the arrows in FIG. 1. At the top of the riser 11 air within the suspension culture is disengaged.

A continuous supply of culture medium is provided through inlet 25. The culture medium includes nutrients and other factors necessary for efficient culture of the cells, and may additionally include between 0.01 to 0.3% (w/v) of a polygalacturonic acid. The use of a polygalacturonic acid promotes flocculation of animal cell and animal cell debris which assists in the efficient separation of animal cells and debris from the product stream. Culture supernatant is continuously withdrawn through outlet 23 at substantially the same rate as culture medium is supplied through inlet 25. In removing culture supernatant from the static settling zone 19, suspension culture is moved from the turbulent environment in downcomer 13 through port 21. The static settling zone 19 is a non-turbulent area in which cells and cell debris, being of a greater density than the culture supernatant, settle downwardly under gravity. The rate of removal of culture supernatant is such that cells within the static settling zone 19 move downwardly and eventually are returned to the downcomer 13 via port 21.

Under steady state conditions a cell concentration gradient is established in the static settling zone 19 allowing removal of culture supernatant through outlet 23 with little or no removal of bulk culture from the suspension culture. The angle of the frustoconical section 7 to the axis of the outer fermenter vessel 1 is between 0° and 60° depending upon the size of static settling zone 19 required by particular operating conditions. Under certain circumstances, for example in fermenters of low volume the outer fermenter vessel 1 may be a single cylindrical vessel and the static zone an area defined by a double-walled divider plate. In the embodiment shown in FIG. 1, the static settling zone 19 is provided with a baffle plate 27 which acts to reduce turbulence within the static settling zone. The angle of the baffle plate to the axis of the fermenter is between 0° and 60° and is, in general, parallel with a corresponding frustoconical section 7. The baffle plate is optional, and if provided extends from a half to the complete vertical distance of the frustoconical section 7. The static settling zone 19 has a cross-sectional area which depends upon the cells cultured in the fermenter. When using mammalian cells the settling zone suitably has a cross-sectional area of between 0.1 and 2.5 $m^2$ per $m^3$ of fermenter volume. Preferably the static settling zone 19 has a cross-sectional area of 0.65 $m^2$ per $m^3$ of fermenter volume.

Figure 2:
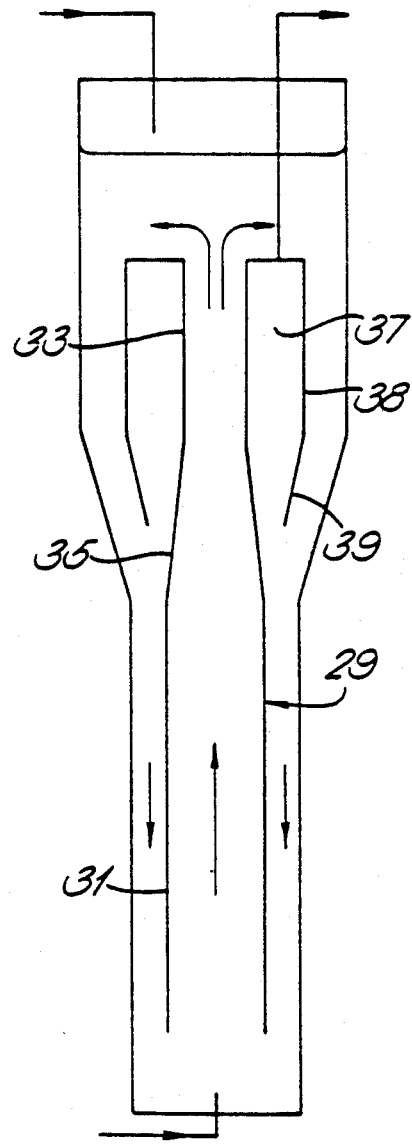
FIG. 2 is an axial cross-section of an air-lift fermenter of the invention including a draught tube concentric with the fermenter vessel and, FIG. 3 is axial cross-section of an air-lift fermenter of the invention including a double-walled concentric draught tube.

Referring to FIG. 2 there is shown a further embodiment of the invention. As is clear from the drawing, the air-lift fermenter shown in FIG. 2 has a number of features in common with the air-lift fermenter described in relation to FIG. 1. These features are not here described further. The difference lies in the use of a draught tube 29 located concentrically within the outer vessel of the fermenter. The inside of the draught tube 29, in use, acts as the riser and the annular space between the outside of the draught tube 29 and the inside of the fermenter vessel acts as the downcomer. In the embodiment shown, the draught tube 29 comprises a lower cylindrical portion 31 and an upper cylindrical portion 33, the two portions being connected by a frustoconical portion 35. The reduction in diameter of the riser towards the top enables a larger cross-sectional area to be used at the upper end of the fermenter for the static settling zone. The static settling zone 37 comprises an annular space formed between the upper end of the draught tube 29 and a surrounding skirt 38 integral therewith. In general the operation and components of the air-lift fermenter shown in FIG. 2 are as described in relation to that of FIG. 1. As with the embodiment of FIG. 1, a baffle plate 39 may be provided at the bottom of the static settling zone 37 to prevent eddy currents. In the embodiment of FIG. 2 the baffle plate 39 is frustoconical. The preferred dimensions mentioned in respect of FIG. 1 apply to the corresponding parts of the air-lift fermenter of FIG. 2.

Figure 3:
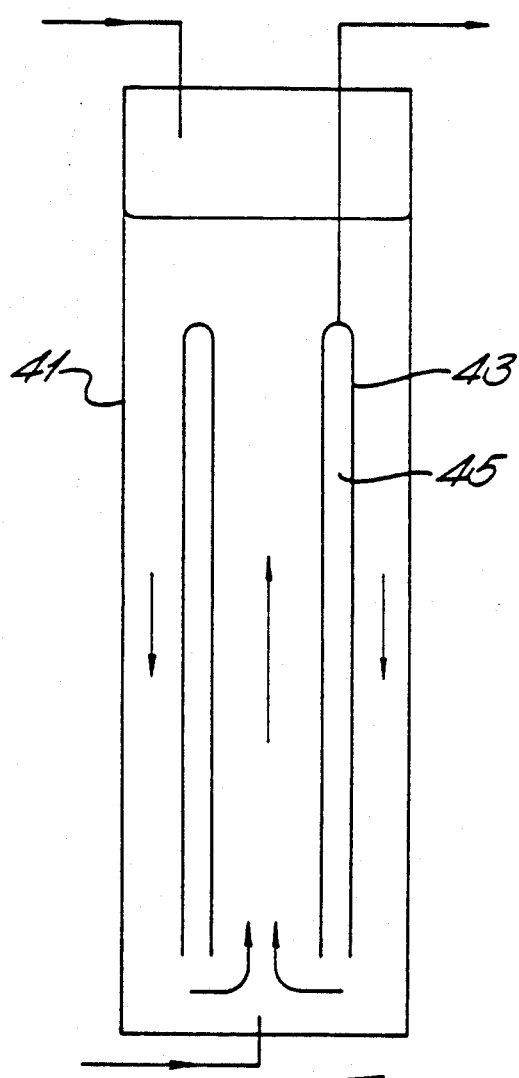

Referring to FIG. 3, an air-lift fermenter is shown which has a configuration especially suitable for low volume use. The air-lift fermenter shown in FIG. 3 comprises a cylindrical outer vessel 41 and a cylindrical draught tube 43 located concentrically within the outer vessel 41. The draught tube 43 is double-walled, an annular space formed between the two walls forming an annular static settling zone 45. The operation and general dimensions of the fermenter of FIG. 3 are as described above with reference to FIG. 1.

The following Examples illustrate the use of a fermenter of the invention for continuous suspension culture of animal cells.

EXAMPLE 1

An existing 5.5 liter (total volume) airlift fermenter was modified so as to permit its use for the cultivation of a suspension of mammalian cells in continuous mode with biomass feedback.

TABLE 1

| | 5 liter airlift fermenter | | | | | | |
|---|---|---|---|---|---|---|---|
| MODE OF OPERATION | MEDIUM FEED RATE FERMENTER VOLUMES/DAY | CELL POPULATION IN CELL CULTURE $\times 10^{-6}$/ml | | CELLS IN OUTFLOW $\times 10^{-6}$/ml | | ANTIBODY CONCENTRATION mg/Liter | ANTIBODY OUTPUT mg/day |
| | | VIABLE | TOTAL | VIABLE | TOTAL | | |
| WITHOUT CELL FEEDBACK | 0.5 | 1.3 | 2.0 | 1.3 | 2.0 | 30.4 | 63 |
| WITH CELL FEEDBACK | 1.0 | 5.3 | 10.4 | 0.6 | 1.5 | 75.2 | 323 |

The fermenter was modified by constructing a double-walled draught tube. The walls of the draught tube were parallel as shown in FIG. 3. The fermenter was fitted with two harvest lines. The first harvest line led from the main bulk of the culture to the outside of the fermenter so that the culture could be harvested continuously without feedback of biomass. The second harvest line led from the top of the draught tube to the outside of the fermenter (FIG. 3) so that the culture fluid could be harvested continuously but with feedback of biomass to the main bulk of the culture.

NB1 hybridoma cells, secreting an IgM antibody, were cultivated in the fermenter described above. Culture medium was Dulbecco's modification Eagle's medium supplemented with foetal calf serum. Dissolved oxygen tension, pH and temperature were monitored and controlled automatically. Cell counts were made using a modified Fuch's Rosenthal counting chamber and cell viability was assessed by exclusion of trypan blue dye. Antibody was assayed by an IgM specific enzyme-linked-immunosorbent assay.

Experimental conditions and results are summarised in Table 1. Without biomass feedback, the viable cell population density was $1.3 \times 10^6$ cells/ml and the antibody concentration was 30.4 mg/liter. With operation of biomass feedback 89% of viable cells were removed from the outflow resulting in a fourfold increase in viable biomass in the culture to $5.3 \times 10^6$ cells/ml. The overall output of antibody was 63 mg/liter during operation without biomass feedback and 323 mg/day during operation with biomass feedback.

EXAMPLE 2

In a second example a 30 liter (total volume) air-lift fermenter was modified for use in continuous mode with biomass feedback. Modifications were similar to those described in Example 1 for the 5 liter fermenter except that two different configurations of draught tube were tested. The first configuration consisted of a parallel-walled draught tube as shown in FIG. 3.

In the second configuration, the draught tube was slightly constricted towards its lower aspect (as shown in FIG. 2) in order to reduce turbulence within the liquid column contained between the draught tube walls.

Cell line, medium and experimental procedures were as described in Example 1, and the results are summarised in Table 2.

Without biomass feedback a viable cell population density of $1.6 \times 10^6$ cells/ml was attained. Under conditions of biomass feedback, viable cell population densities were $6.0 \times 10^6$ cells/ml for the parallel-walled draught tube, and $3.5 \times 10^6$ cells/ml for the draught tube with constricted aperture. Antibody output was 325 mg/day during operation without biomass feedback and 630 mg/day during operation with feedback.

It will be understood that the present invention has been described above purely by way of example, and modifications of detail can be made within the scope and spirit of the invention.

What is claimed is:

1. A continuous fermentation device for receiving a suspension culture of cells, the device comprising:
   a fermentation vessel having inlet means to deliver suspension culture medium;
   baffle means defining, in combination with interior walls of said vessel, a downcomer and a riser;
   pump means for forcing a suspension culture to circulate in the riser and downcomer;
   a portion of said baffle means further defining a static settling zone disposed within said vessel, wherein said zone is surrounded by at least one of said riser and said downcomer, said zone having a bottom opening communicating with at least one of said riser and downcomer, and a top opening connected to outlet means to draw off culture supernatant, and wherein said zone provides for cells to settle out in its bottom so as to result in a cell concentration lower in the supernatant than in the suspension.

TABLE 2

| | 30 Liter Airlift Fermenter | | | | | | |
|---|---|---|---|---|---|---|---|
| MODE OF OPERATION | MEDIUM FEED RATE FERMENTER VOLUMES/DAY | CELL POPULATION $\times 10^{-6}$/ml | | CELLS IN OUTFLOW $\times 10^{-6}$ml | | ANTIBODY CONCENTRATION mg/Liter | ANTIBODY OUTPUT mg/day |
| | | VIABLE | TOTAL | VIABLE | TOTAL | | |
| WITHOUT CELL FEEDBACK | 0.5 | 1.6 | 2.3 | 1.6 | 2.3 | 26 | 325 |
| WITH CELL FEEDBACK (parallel-walled draught tube | 0.7 | 6.0 | 8.0 | 1.0 | 2.5 | 30 | 630 |
| With cell feedback (constricted draught tube | 0.7 | 3.5 | 5.0 | 1.0 | 1.6 | not done | — |

2. The continuous fermentation device according to claim 1, wherein said zone is disposed in said vessel such that the zone may be submerged in suspension culture to a depth of at least 0.25 to 1.0 times a width of the vessel.

3. The continuous fermentation device according to claim 1, wherein said pump means comprises an air injector located lowermost in said vessel.

4. The continuous fermentation device according to claim 1, wherein said baffle means comprises a cylindrical draught tube.

5. The continuous fermentation device according to claim 4, wherein said zone has an annular shape.

6. The continuous fermenter device according to claim 5, wherein said baffle means further comprises means for preventing eddy currents, which means is a baffle plate having a frustoconical cross-section and extending from said portion of said baffle means which defines said static settling zone toward said bottom opening.

7. The continuous fementation device according to claim 1, wherein said baffle means comprises a vertically disposed plate.

8. The continuous fermenter device according to claim 7, wherein said buffle means further comprises means for preventing eddy currents, which means is a baffle plate having a frustoconical cross-section and extending from said portion of said baffle means which defines said static settling zone toward said bottom opening.

9. A method for the suspension culture of cells, comprising:
   culturing cells in a continuous fermentation device, wherein the device comprises:
   a fermentation vessel having inlet means to deliver suspension culture medium;
   baffle means defining, in combination with interior walls of said vessel, a downcomer and a riser;
   pump means for forcing a suspension culture of cells to circulate in the riser and downcomer;
   a portion of said baffle means further defining a static settling zone disposed within said vessel, wherein said zone is surrounded by at least one of said riser and said downcomer, said zone having a bottom opening communicating with at least one of said riser and downcomer, and a top opening connected to outlet means to draw of culture supernatant, and wherein said zone provides for cells to settle out its bottom so as to result in a cell concentration lower in the supernatant than in the suspension.

10. The method according to claim 9, wherein the cells are hybridoma cells.

* * * * *